US008087113B2

(12) United States Patent
Roff et al.

(10) Patent No.: US 8,087,113 B2
(45) Date of Patent: Jan. 3, 2012

(54) INFLATABLE SUPPORT

(75) Inventors: Simon Michael Roff, Dunstable (GB);
Christopher Rowe, Aylesbury (GB)

(73) Assignee: Hunteigh Technology Limited (GB)

( * ) Notice: Subject to any disclaimer, the term of this patent is extended or adjusted under 35 U.S.C. 154(b) by 0 days.

(21) Appl. No.: 12/211,507

(22) Filed: Sep. 16, 2008

(65) Prior Publication Data
US 2009/0007341 A1    Jan. 8, 2009

Related U.S. Application Data

(63) Continuation of application No. 10/507,958, filed on May 12, 2005, now abandoned.

(51) Int. Cl.
*A47C 27/10* (2006.01)
(52) U.S. Cl. .................................. 5/713; 5/706
(58) Field of Classification Search .............. 5/710–713, 5/706, 691
See application file for complete search history.

(56) References Cited

U.S. PATENT DOCUMENTS

| 5,117,518 A | 6/1992 | Schild | |
|---|---|---|---|
| 5,189,742 A | 3/1993 | Schild | |
| 5,539,942 A * | 7/1996 | Melou | 5/655.3 |
| 5,651,151 A | 7/1997 | Schild | |
| 5,873,137 A * | 2/1999 | Yavets-Chen | 5/713 |
| 6,058,537 A * | 5/2000 | Larson | 5/710 |
| 6,058,538 A | 5/2000 | Fletcher | |
| 6,098,222 A | 8/2000 | Chambers et al. | |
| 6,212,718 B1 | 4/2001 | Stolpmann et al. | |
| 6,253,401 B1 | 7/2001 | Boyd | |
| 6,412,129 B1 | 7/2002 | Wu | |
| 6,877,178 B2 * | 4/2005 | Chapman et al. | 5/713 |
| 7,038,419 B1 | 5/2006 | Beale et al. | |

FOREIGN PATENT DOCUMENTS

| EP | 0 560 563 A | 9/1993 |
|---|---|---|
| GB | 2 307 402 A | 5/1997 |
| WO | WO 01/09695 A | 2/2001 |

* cited by examiner

*Primary Examiner* — Fredrick Conley
(74) *Attorney, Agent, or Firm* — Craig A. Fieschko, Esq.; DeWitt Ross & Stevens S.C.

(57) ABSTRACT

An alternating pad comprises a first set and a second set of alternately inflatable cells. Both sets of inflatable cells are supplied with air from a pump via a rotary valve. A sensor is positioned under the pad to receive pressure exerted by a patient upon movement and to be compressible relative to the applied pressure. Any change in patient position or movement will cause an alteration in the airflow in the sensor pad tube and will reduce or increase the differential pressure measured at the pressure transducer. Based on this feedback the microprocessor directly controls the power level to the pump and increases or decreases the air flow to the cells to alter the amplitude of the cells and also controls the timing of the rotary valve to change the timing of the inflation and deflation cycle.

11 Claims, 3 Drawing Sheets

INFLATABLE SUPPORT

CROSS-REFERENCE TO RELATED APPLICATIONS

This application is a continuation of U.S. patent application Ser. No. 10/507,958 filed May 12, 2005, now abandoned which is incorporated by reference herein.

BACKGROUND OF THE INVENTION

This invention relates to an inflatable support, in particular an inflatable support that measures the movements of a patient supported on the support and adjusts the support provided depending on the movements detected.

There have been several techniques developed to measure body movement, patient entry and patient exit from a support using fluctuations in air pressure in the inflatable supports or inflatable bodies inserted between the patient and a supporting surface. The technique of measuring body movements by recording the air pressure in an air filled pad placed under a mattress was described by Kusunoki (1985). Another system has been developed to measure the respiratory movements of subjects by measuring pressure changes in a supporting air mattress (Hernandez 1995). U.S. Pat. No. 6,036,660 describes a system that uses transducers to detect and display movement in an air-filled cell or cells between a patient and a support.

Overall, these systems give a numerical or visual display of detected movement using the fluctuation of static air in an enclosed cell or cells. As there is a link between the rate of spontaneous body movements and the risk of developing pressure sores (Exton-Smith et al, 1961), the information provided or displayed helps in the assessment of the risk of pressure sore development. The information can be used to increase the manual turning of the patient or to aid the decision to move the patient to another support surface. Equally, the information can be completely ignored in a busy ward.

SUMMARY OF THE INVENTION

The invention includes an inflatable support whose inflation and/or deflation regime is automatically controlled in dependence upon the movement of a patient on the support. In this way, patient comfort and pressure relief is automatically optimized without requiring external input from a carer or nurse.

Accordingly, the invention includes an inflatable support supplied with air from a pump by means of valve, a sensor positioned under the support to measure the movements of a patient on the support, and control means adjusting the inflation and/or deflation of the support by the pump in response to the measurement values from the sensor. Thus, where a patient is able to move by themselves on a regular basis on an inflatable mattress, the pressures at which the mattress is inflated can be adjusted to improve comfort without increasing the risk of pressure sore development.

In an alternating pressure mattress, there is a compromise between an effective alternating pressure cycle used to reduce the risk of pressure sore development and the comfort experienced by the patient. Preferably, the inflatable support is an alternating inflatable support and more preferably, the control means adjusts the inflation and/or deflation pressures and cycle times of the support in response to the measurement values from the sensor.

Therefore, where a patient is able to move by themselves on a regular basis on an alternating mattress, the inflation/deflation cycle parameters can be altered to improve comfort without increasing the risk of pressure sore development. For example, a device in accordance with the present invention can lengthen the cycle time to provide extra comfort for those patients who are making significant autonomous movements, or shorten the time for those patients that require more active pressure relief.

Preferably, a display of the patient movement is also provided. Many of the risk assessment tools (Waterlow, Norton & Braden) use movement as part of their scoring system and an accurate movement display assists nurses in selecting the correct support surface.

BRIEF DESCRIPTION OF THE DRAWINGS

An embodiment of the present invention is described below, by way of example only, with reference to the accompanying drawings, in which.

DETAILED DESCRIPTION OF THE PREFERRED EMBODIMENT(S)

Figure 1:
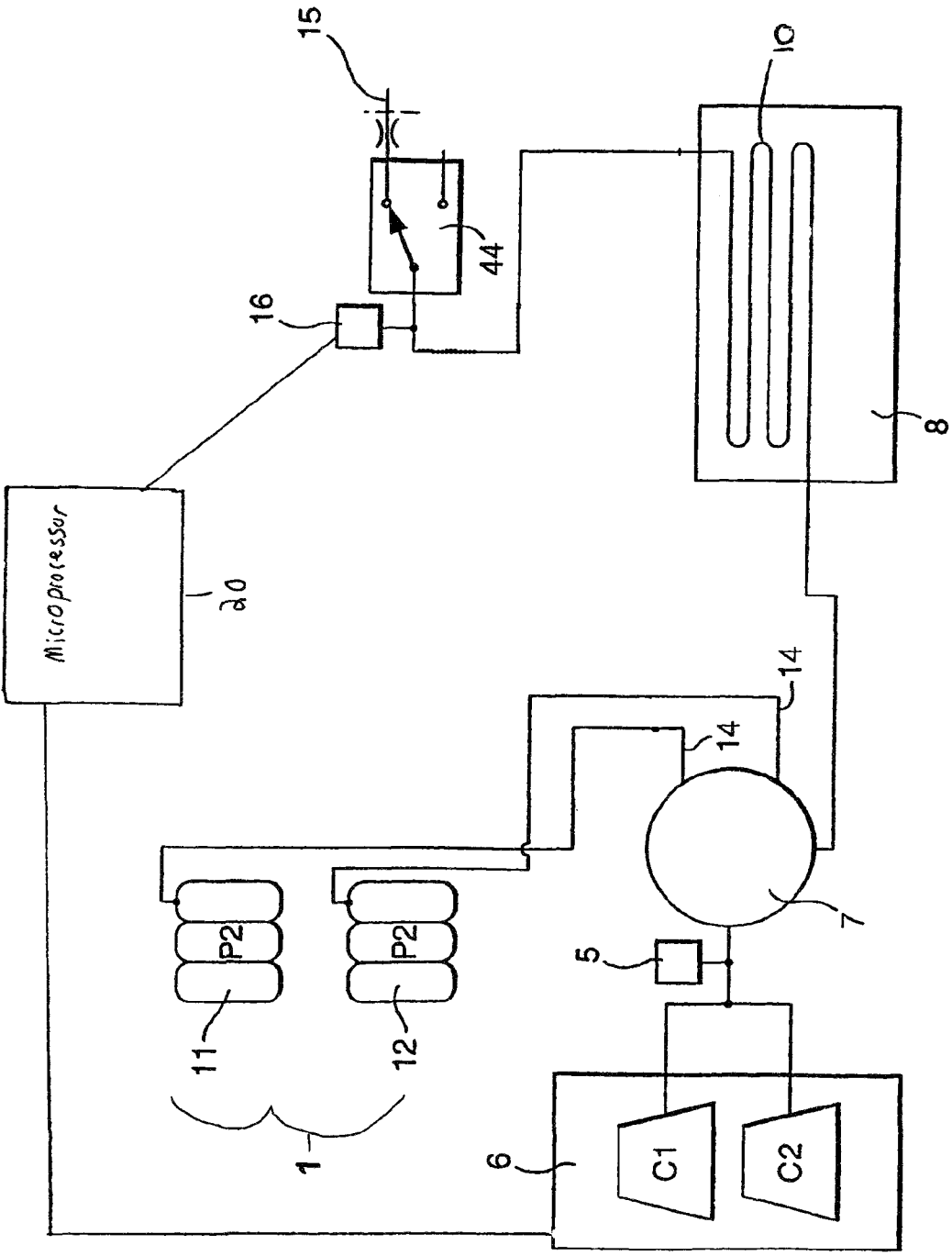
FIG. 1 is a schematic diagram of a support according to the invention.
Figure 2:
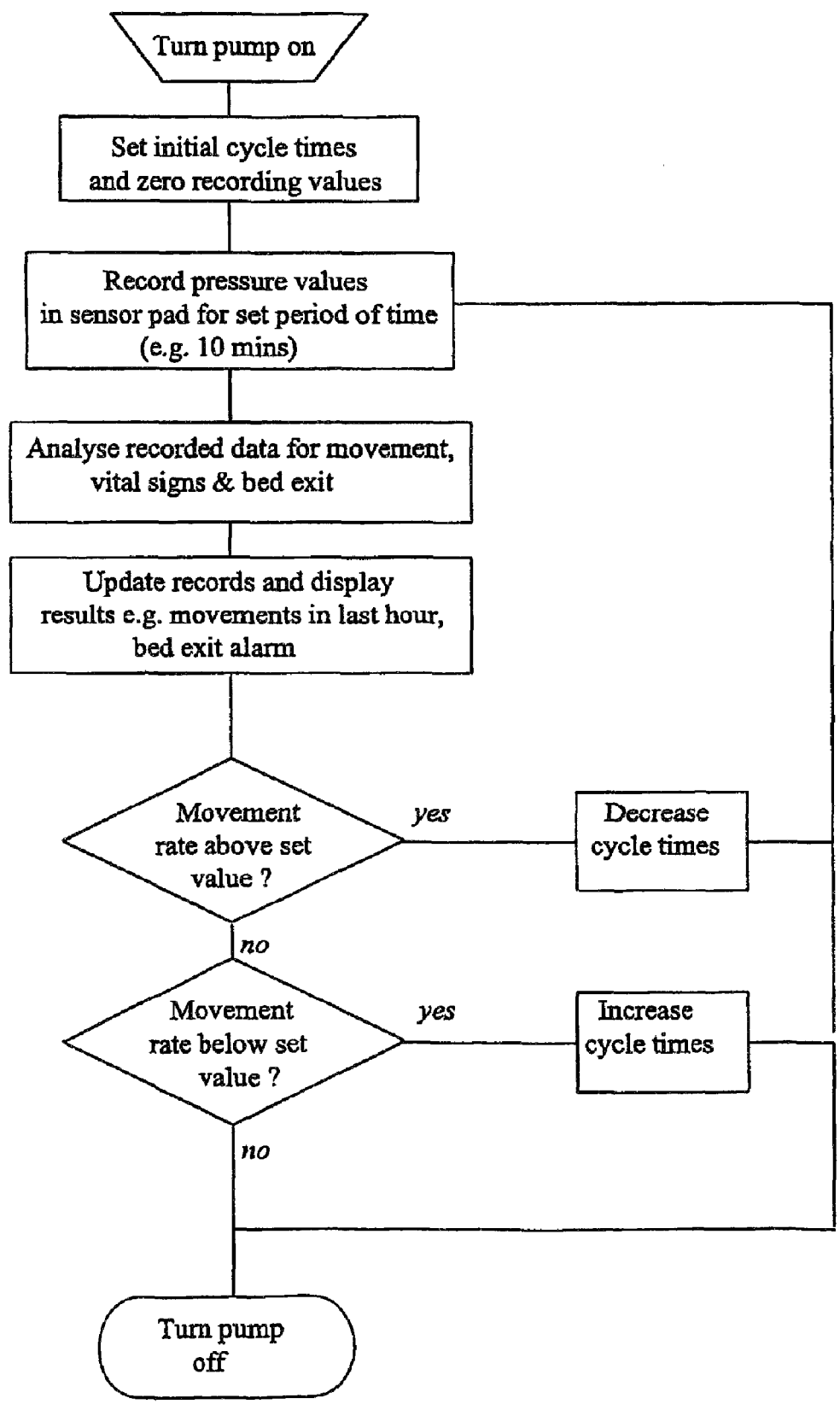
FIG. 2 is a flow chart showing a control algorithm according to the invention.

Referring to FIG. 1, an alternating pad 1 is shown comprising a first set 11 and a second set 12 of alternately inflatable cells. Both sets of inflatable cells are supplied with air from a pump 6 via a rotary valve 7. A pair of air supply lines 14 lead from the rotary valve 7 to the pad 1.

A tube 10 of a sensor 8 is connected at one end to the output of the pump 6 and at the other end to a solenoid 44, pressure transducer 16 and a restrictor 15. The sensor 8 is positioned under the pad 1 to receive pressure exerted by a patient upon movement and to be compressible relative to the applied pressure.

In use, the pump 6 delivers air to the pad 1 by means of a rotary valve 7 so that each set of cells 11, 12 of the pad 1 is alternately inflated and deflated. A pressure transducer 5 is used to check the pressure of the output from the pump 6. The system operates on an inflation/deflation cycle repeating over periods varying from two minutes to over twenty minutes.

During the inflation cycle, the rotary valve 7 is in such a position that a portion of the flow goes via the tube 10 and the rest fills the cells 11 or 12 depending on the cycle. Any change in patient position or movement will cause an alteration in the airflow in the sensor pad tube 10 and will reduce or increase the differential pressure measured at the pressure transducer 16. Based on this feedback a microprocessor 20 directly controls the power level to pump 6 and therefore the compressor(s) C1, C2 pneumatic output, thus increasing or decreasing the air flow to the cells 11, 12 to alter the amplitude of the cells 11, 12 and control the timing of the rotary valve 7 to change the timing of the inflation and deflation cycle.

Sensor air flow through tube 10 is measured via the differential pressure across the restrictors 15. The differential pressure is measured by pressure transducer 16 by comparison to atmospheric pressure.

The pressure recordings at the exit of sensor 8, because of fluctuations in the air within the sensor 8, are measured and the movements analyzed, the control means or microprocessor 20 then controls the rotary valve 7, and thus the timing of the pressure cycle in response to the movements detected.

Preferably, the detected movement values are also displayed on a display panel (see FIGS. 3a, 3b) on the pump 6.

Figure 3A:
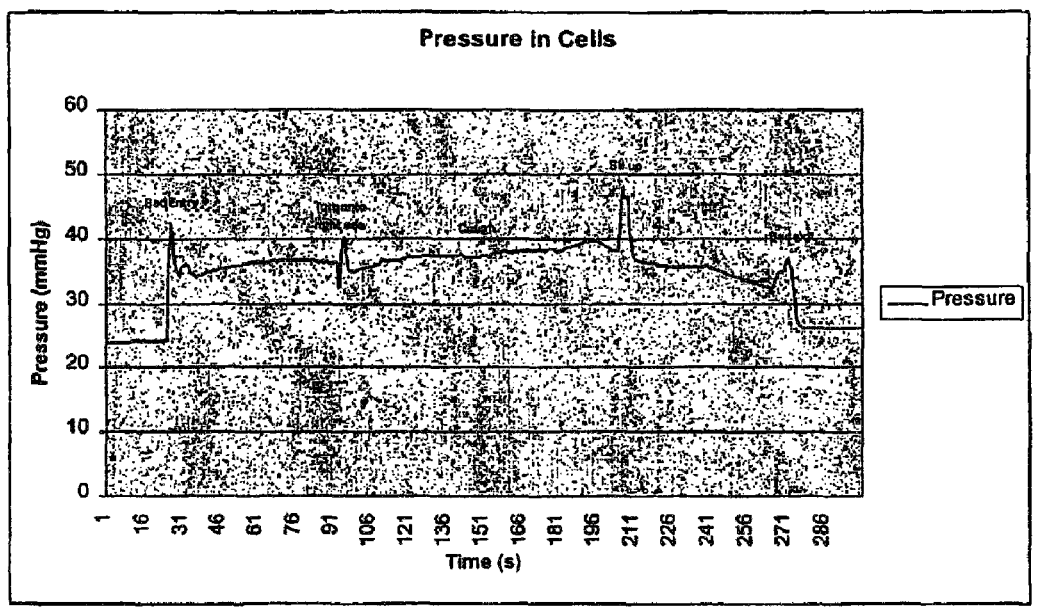
FIGS. 3a and 3b show displays of various body movements measured according to the invention.
Figure 3B:
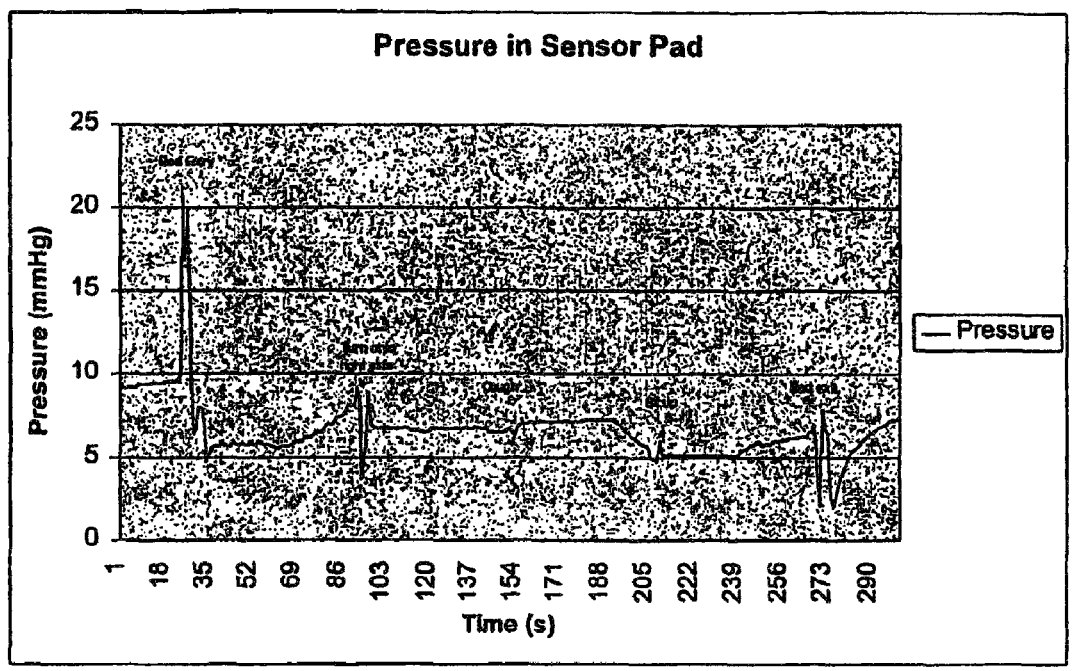

As shown in FIGS. 3a and 3b, the pressure transducer 16 recordings can distinguish between the various types of movements, including large and small body movements, patient exit and patient location. A windowing technique is used to detect the various movement parameters.

The large body movements indicate a significant change in body position with a subsequent redistribution of body weight. If the large body movements are within normal levels, for example, one large movement every ten minutes, then the frequency of the flow cycle is reduced, increasing the comfort to the patient. The frequency is increased when there are no large body movements detected.

The patient exit is detected by sudden large changes in the pressure, or by comparison of the pressures between consecutive cycles.

Additionally, the pad 1 can be segmented into zones for a heel section, an upper leg section, a mid torso section, and a head section. The sections can be inflated at differing amplitudes for comfort and reduced risk of pressure sore development.

Although the particular embodiment described above relates to an alternating pressure pad 1, the invention applies equally to a static pressure pad with a sensor and further a pad having a zoned head, upper leg, torso and heel sections.

The pump 6 may use powered pulse width modulated (PWM) driven compressors as opposed to the mains alternating current driven compressors of the prior art. The microprocessor 20 creates the driving waveform for the compressors C1, C2 with variable mark space constant repetition rate and constant amplitude, so that the pump 6 is not dependent for performance on any particular mains voltage or frequency. Therefore, the pump 6 can be operated from the mains voltage of any country. The compressors output is varied by varying the PWM mark space ratio from zero to maximum.

The sensor 8 and microprocessor 20 can be used to display the number of times the patient has moved on the support and sound an alarm if the patient has not moved or initiate contact with a third party by means of conventional communications devices.

The invention claimed is:

1. A method for inflating a patient support pad having inflatable cells therein, the method including the steps of:
   a. providing fluid to the cells of the pad, each cell having successive inflation/deflation cycles wherein each cycle includes:
      (1) a period over which fluid is supplied to the cell, and
      (2) a period over which fluid is released from the cell, with the successive inflation/deflation cycles:
         i. defining a supply frequency, and
         ii. being out of phase between different cells;
   b. accumulating a count of a number of pressure changes in the pad which are representative of successive movements of the patient on the pad, the count being accumulated over at least the period over which fluid is supplied to the pad;
   c. adjusting the supply frequency in response to both:
      (1) the number of pressure changes representative of patient movements, and
      (2) the time over which the number of pressure changes representative of patient movements occur.

2. The method of claim 1 wherein the pressure changes counted in the pad are pressure changes occurring at rates greater than the supply frequency.

3. The method of claim 1 wherein the step of adjusting the supply frequency includes:
   a. if the number of pressure changes representative of patient movements is greater than a set value, decreasing the supply frequency; and
   b. if the number of pressure changes representative of patient movements is are less than a set value, increasing the supply frequency.

4. The method of claim 1 wherein the step of adjusting the supply frequency to the pad includes adjusting the times at which fluid is supplied to the different ones of the cells.

5. The method of claim 1 wherein the change in pressure in the pad over time is measured by a sensor situated beneath and outside of the pad.

6. A method for inflating an inflatable patient support pad, the pad having inflatable cells therein, the method including the steps of:
   a. cyclically inflating and deflating the cells at a supply frequency, wherein different cells are inflated at different times;
   b. measuring the rate of patient movement atop the cells; and
   c. adjusting the supply frequency in response to the measured rate of patient movement.

7. The method of claim 6 wherein the step of measuring the rate of patient movement atop the cells includes accumulating a count of pressure changes within the cells over time.

8. The method of claim 7 wherein the step of adjusting the supply frequency is performed when the accumulated count of pressure changes measured within the cells occur at a rate substantially greater than the supply frequency.

9. The method of claim 6 wherein the step of measuring the rate of patient movement atop the cells includes measuring pressure changes within the cells occurring at a rate greater than the supply frequency.

10. The method of claim 6 wherein:
    a. the supply frequency is decreased if the rate of patient movement increases; and
    b. the supply frequency is increased if the rate of patent movement decreases.

11. The method of claim 6 wherein the times at which the cells are inflated are varied in response to the measured rate of patient movement.

* * * * *